(12) United States Patent
Zaddem et al.

(10) Patent No.: US 7,527,588 B2
(45) Date of Patent: May 5, 2009

(54) SYSTEM AND METHOD FOR SURGICAL IMPLANT PLACEMENT

(75) Inventors: Vincenza Zaddem, Easton, PA (US); Mark Howansky, Union City, NJ (US); Jessica Liberatore, Marlboro, NJ (US); Gene W. Kammerer, East Brunswick, NJ (US); Jacqueline Flatow, Vacaville, CA (US)

(73) Assignee: Ethicon, Inc., Somerville, NJ (US)

( * ) Notice: Subject to any disclaimer, the term of this patent is extended or adjusted under 35 U.S.C. 154(b) by 929 days.

(21) Appl. No.: 10/941,241

(22) Filed: Sep. 15, 2004

(65) Prior Publication Data
US 2006/0058575 A1  Mar. 16, 2006

(51) Int. Cl.
*A61F 2/00* (2006.01)
(52) U.S. Cl. .......................................... 600/29; 600/37
(58) Field of Classification Search ............. 600/29–32, 600/37; 128/DIG. 25, 885, 897–899; 606/119, 606/139, 148, 151, 222–225
See application file for complete search history.

(56) References Cited

U.S. PATENT DOCUMENTS

| 3,182,662 | A | 5/1965 | Shirodkar |
| 3,212,502 | A | 10/1965 | Myers |
| 3,311,110 | A | 3/1967 | Singerman |
| 3,372,695 | A | 3/1968 | Beliveau et al. |
| 3,472,232 | A | 10/1969 | Earl |
| 3,608,095 | A | 9/1971 | Barry |
| 3,763,860 | A | 10/1973 | Clarke |
| 3,858,783 | A | 1/1975 | Kapitanov et al. |
| 3,924,633 | A | 12/1975 | Cook et al. |
| 4,037,603 | A | 7/1977 | Wendorff |
| 4,128,100 | A | 12/1978 | Wendorff |
| 4,235,238 | A | 11/1980 | Ogiu et al. |
| 4,392,495 | A | 7/1983 | Bayers |
| 4,441,497 | A | 4/1984 | Paudler |
| 4,509,516 | A | 4/1985 | Richmond |
| 4,549,545 | A | 10/1985 | Levy |

(Continued)

FOREIGN PATENT DOCUMENTS

AU  278089 B  6/1965

(Continued)

OTHER PUBLICATIONS

Leanza, V. et al. New Technique For Correcting Both Incontinence And Cystocele: T.I.C.T. (Tension-Free Incontinence Cystocele Treatment) Urogynaecologia International Journal, 2001, No. 3515, pp. 133-140.

(Continued)

*Primary Examiner*—John P Lacyk (57) ABSTRACT

A system and method for placing surgical implants and having particular application for pelvic floor repair. The system includes an assembly having a guide element with a tissue penetrating tip, a cannula, and a retrieval device having a capture element at its distal end. A channel in the cannula is dimensioned to allow passage therethrough of the guide element, and of the retrieval element when removably coupled with an extension of the surgical implant.

17 Claims, 10 Drawing Sheets

U.S. PATENT DOCUMENTS

| | | | |
|---|---|---|---|
| 4,736,746 A | 4/1988 | Anderson |
| 4,930,674 A | 6/1990 | Barek |
| 4,946,467 A | 8/1990 | Ohi et al. |
| 5,013,292 A | 5/1991 | Lemay |
| 5,032,508 A | 7/1991 | Naughton et al. |
| 5,080,667 A | 1/1992 | Chen et al. |
| 5,112,344 A | 5/1992 | Petros |
| 5,180,385 A | 1/1993 | Sontag |
| 5,250,033 A | 10/1993 | Evans et al. |
| 5,281,237 A | 1/1994 | Gimpelson |
| 5,337,736 A | 8/1994 | Reddy |
| 5,361,782 A | 11/1994 | Bauer |
| 5,362,294 A | 11/1994 | Seitzinger |
| 5,368,595 A | 11/1994 | Lewis |
| 5,368,756 A | 11/1994 | Vogel et al. |
| 5,370,294 A | 12/1994 | Bauer |
| 5,382,257 A | 1/1995 | Lewis et al. |
| 5,383,904 A | 1/1995 | Totakura et al. |
| 5,403,328 A | 4/1995 | Shallman |
| 5,441,508 A | 8/1995 | Gazielly et al. |
| 5,450,860 A | 9/1995 | O'Connor |
| 5,503,638 A | 4/1996 | Cooper et al. |
| 5,507,796 A | 4/1996 | Hasson |
| 5,520,700 A | 5/1996 | Beyar et al. |
| 5,540,240 A | 7/1996 | Bauer |
| 5,582,188 A | 12/1996 | Benderev et al. |
| 5,611,515 A | 3/1997 | Benderev et al. |
| 5,628,756 A | 5/1997 | Barker, Jr. et al. |
| 5,645,568 A | 7/1997 | Chervitz et al. |
| 5,741,299 A | 4/1998 | Rudt |
| 5,755,728 A | 5/1998 | Maki et al. |
| 5,807,403 A | 9/1998 | Beyar et al. |
| 5,816,258 A | 10/1998 | Jervis |
| 5,836,315 A | 11/1998 | Benderev et al. |
| 5,840,011 A | 11/1998 | Landgrebe et al. |
| 5,855,549 A | 1/1999 | Newman |
| 5,860,425 A | 1/1999 | Benderev et al. |
| 5,899,909 A | 5/1999 | Claren et al. |
| 5,899,999 A | 5/1999 | De Bonet |
| 5,934,283 A | 8/1999 | Willem et al. |
| 5,935,122 A | 8/1999 | Fourkas et al. |
| 5,945,122 A | 8/1999 | Abra et al. |
| 5,972,000 A | 10/1999 | Beyar |
| 5,997,554 A | 12/1999 | Thompson |
| 6,010,447 A | 1/2000 | Kardjian |
| 6,030,393 A | 2/2000 | Corlew |
| 6,042,534 A | 3/2000 | Gellman et al. |
| 6,042,536 A | 3/2000 | Tihon et al. |
| 6,068,591 A | 5/2000 | Bruckner et al. |
| 6,110,101 A | 8/2000 | Tihon et al. |
| 6,117,067 A | 9/2000 | Gil-Verrnet |
| 6,190,401 B1 | 2/2001 | Green et al. |
| 6,197,036 B1 | 3/2001 | Tripp et al. |
| 6,221,005 B1 | 4/2001 | Bruckner et al. |
| 6,273,852 B1 | 8/2001 | Lehe et al. |
| 6,306,079 B1 | 10/2001 | Trabucco |
| 6,334,446 B1 | 1/2002 | Beyar |
| 6,382,214 B1 | 5/2002 | Raz et al. |
| 6,406,423 B1 | 6/2002 | Scetbon |
| 6,475,139 B1 | 11/2002 | Miller |
| 6,478,727 B2 | 11/2002 | Scetbon |
| 6,491,703 B1 | 12/2002 | Ulmsten |
| 6,494,887 B1 | 12/2002 | Kaladelfos |
| 6,575,897 B1 | 6/2003 | Ory et al. |
| 6,575,984 B2 | 6/2003 | Beyar |
| 6,575,998 B2 | 6/2003 | Beyar |
| 6,592,610 B2 | 7/2003 | Beyar |
| 6,595,911 B2 | 7/2003 | LoVuolo |
| 6,605,097 B1 | 8/2003 | Lehe et al. |
| 6,612,977 B2 | 9/2003 | Staskin et al. |
| 6,652,450 B2 | 11/2003 | Neisz et al. |
| 6,691,711 B2 | 2/2004 | Raz et al. |
| 6,692,506 B1 | 2/2004 | Ory et al. |
| 6,802,807 B2 | 10/2004 | Anderson et al. |
| 6,808,486 B1 | 10/2004 | O'Donnell |
| 6,808,487 B2 | 10/2004 | Migliari |
| 6,830,052 B2 | 12/2004 | Carter et al. |
| 2001/0018549 A1 | 8/2001 | Scetbon |
| 2001/0049467 A1 | 12/2001 | Lehe et al. |
| 2002/0028980 A1 | 3/2002 | Thierfelder et al. |
| 2002/0058959 A1 | 5/2002 | Gellman |
| 2002/0077526 A1 | 6/2002 | Kammerer et al. |
| 2002/0091373 A1 | 7/2002 | Berger |
| 2002/0099258 A1 | 7/2002 | Staskin et al. |
| 2002/0099259 A1 | 7/2002 | Anderson et al. |
| 2002/0107430 A1 | 8/2002 | Neisz et al. |
| 2002/0147382 A1 | 10/2002 | Neisz et al. |
| 2002/0151762 A1 | 10/2002 | Rocheleau et al. |
| 2002/0161382 A1 | 10/2002 | Neisz et al. |
| 2002/0188169 A1 | 12/2002 | Kammerer et al. |
| 2003/0023137 A1 | 1/2003 | Gellman |
| 2003/0023138 A1 | 1/2003 | Luscombe |
| 2003/0036676 A1 | 2/2003 | Scetbon |
| 2003/0045892 A1 | 3/2003 | Kaladelfos |
| 2003/0050530 A1 | 3/2003 | Neisz et al. |
| 2003/0062052 A1 | 4/2003 | Carter et al. |
| 2003/0078468 A1 | 4/2003 | Skiba et al. |
| 2003/0149440 A1 | 8/2003 | Kammerer et al. |
| 2003/0171644 A1 | 9/2003 | Anderson et al. |
| 2003/0176762 A1 | 9/2003 | Kammerer |
| 2003/0176875 A1 | 9/2003 | Anderson et al. |
| 2003/0191360 A1 | 10/2003 | Browning |
| 2003/0195386 A1 | 10/2003 | Thierfelder et al. |
| 2003/0212305 A1 | 11/2003 | Anderson et al. |
| 2003/0220538 A1 | 11/2003 | Jacquetin |
| 2004/0015048 A1 | 1/2004 | Neisz et al. |
| 2004/0039453 A1 | 2/2004 | Anderson et al. |
| 2004/0068159 A1 | 4/2004 | Neisz et al. |
| 2004/0106845 A1 | 6/2004 | Anderson et al. |
| 2004/0225181 A1 | 11/2004 | Chu et al. |
| 2004/0243166 A1 | 12/2004 | Odermatt et al. |
| 2004/0249240 A1 | 12/2004 | Goldman et al. |
| 2004/0249397 A1 | 12/2004 | Delorme et al. |

FOREIGN PATENT DOCUMENTS

| | | |
|---|---|---|
| AU | 441561 B | 1/1972 |
| DE | 4334419 A1 | 4/1995 |
| EP | 0 598 976 A2 | 6/1994 |
| EP | 0 774 240 B1 | 5/1997 |
| EP | 0941712 A1 | 9/1999 |
| EP | 1025811 A | 8/2000 |
| SE | 503271 C2 | 4/1996 |
| WO | WO 90/03766 A1 | 4/1990 |
| WO | WO 96/06567 A1 | 3/1996 |
| WO | WO 96/06597 | 3/1996 |
| WO | WO 97/13465 | 4/1997 |
| WO | WO 98/31301 A1 | 7/1998 |
| WO | WO 01/06951 A1 | 2/2001 |
| WO | WO 02/38079 | 5/2002 |
| WO | WO 2004/008977 A | 1/2004 |
| WO | WO 2004/012626 A1 | 2/2004 |

OTHER PUBLICATIONS

Collinet, P., et al., "The Vaginal Patch For Vaginal Cure of Cystocele", J. Gynecol. Obstet. Biol. Reprod./vol. 29, No. 2, 2000, pp. 197-201.

Cosson, M. et al., "Cystocele Repair By Vaginal Patch",, Progres en Urologie, 2001, 11, pp. 340-346.

Petros, P.E. Papa, "Vault Prolapse II:Restoration of Dynamic Vaginal Supports by Infracoccygeal Sacropexy, an Axial Day-Case Vaginal Procedure". International Urogynecol Journal (2001) vol. 12, pp. 296-303, Springer-Verlag London Ltd.

Petros, P.E. Papa, "Vault Prolapse 1: Dynamic Supports of the Vagina", International Urogynecol Journal (2001) vol. 12, pp. 292-295, Springer-Verlag London Ltd.

"AMS Sparc™ Sling System", American Medical Systems, Inc., Minnetonka, MN, 2001, pp. 1-7.

"TVT Tension-free Vaginal Tape, Minimally Invasive Highly Effective Treatment for Female Stress Urinary Incontinence", Gynecare, Ethicon, Inc., 1999, pp. 1-6.

SYSTEM AND METHOD FOR SURGICAL IMPLANT PLACEMENT

FIELD OF THE INVENTION

This invention relates generally to systems and methods for placing surgical implants, and has particular application to placing implants for pelvic floor reconstructive surgery.

DESCRIPTION OF THE PRIOR ART

The use of synthetic and/or biologic meshes in the surgical repair of damaged fascial tissue, such as hernias, has been widely described in literature and patent filings. Recently, attention has been focused on the application of these materials and techniques to the repair of female pelvic floor defects, such as cystocele, rectocele, enterocele and vault prolapse. Unfortunately, surgical procedures developed to address these defects have not demonstrated the same levels of consistent clinical success as predicate established areas of surgical application.

Several factors are believed to contribute to the sub-optimal results seen in the field of pelvic floor repair. First, the anatomy of the pelvic floor is complex and variable, particularly in the presence of fascial defects. Known surgical procedures also require an extremely high level of surgical skill, as surgeons often must gain access deep into the pelvic cavity from a trans-vaginal approach. Further, many pelvic floor repair surgeries require cutting and dissection in very close proximity to critical structures such as the bladder, rectum, peritoneum and a variety of significant vasculature and nerve structures. Suturing deep within the pelvic cavity is also difficult and time consuming, and is often utilized due to the absence of other clinically-supported standardized repair procedures. Finally, instrumentation specifically designed for such surgical procedures is also lacking, forcing surgeons to use instruments designed for other procedures.

Some recent procedures have attempted to address some of the concerns set forth above. U.S. patent Publication No. 2003/0220538, which is incorporated herein by reference in its entirety, describes a standardized procedure and associated implant design that is designed for use in a variety of pelvic floor repair procedures. The described procedure eliminates the need for securing the implant by suturing by providing strap-like mesh extensions that pass through the sacrospinous ligament and/or obturator membrane. U.S. patent Publication No. 2004/0039453 also describes a strap-based implant system for the treatment of a cystocele. Difficulties have been encountered, however, in pulling the strap-like mesh extensions through the pelvic cavity. In particular, the mesh extensions can cause tearing of tissue as they are pulled through, which can cause additional pain, bleeding, and/or nerve damage, but can also lead to improper positioning of the implant.

Accordingly, what is needed is improved instrumentation specifically designed to facilitate, simplify and make more consistent the placement of implants in such procedures.

OBJECTS AND SUMMARY OF THE INVENTION

The present invention provides an assembly for placement of a surgical implant having at least one implant extension portion. The assembly includes a guide element having a tissue penetrating distal end, a cannula having a proximal end, a distal end, and a channel extending therethrough within which the guide element can be slidably received such that the tissue penetrating tip of the guide element extends outward from the distal end of the cannula, and a retrieval device having a capture element at a distal end thereof for coupling with the implant extension portion of the surgical implant. When the cannula has the guide element slidably received therein, it is dimensioned to extend through a patient's pelvic cavity from an external incision and out through a vaginal incision, and the cannula channel is dimensioned allow passage therethrough of the retrieval device and coupled implant extension portion.

The present invention also provides a method for placing a surgical implant including the steps of providing an assembly including a guide element having a tissue penetrating distal end, a cannula having a proximal end, a distal end, and a channel extending therethrough, and a retrieval device having a capture element at a distal end thereof. The method further includes the steps of slidably inserting the guide element into the cannula channel until the tissue penetrating tip extends out of the distal end of the cannula, passing the cannula and guide element through a first passage through a patient's pelvic cavity from an external incision until the distal ends of the guide element and cannula extend out through a vaginal incision, removing the guide element from the cannula by retracting it through the cannula channel, inserting the retrieval device through the cannula channel until the capture element passes out the distal end of the cannula, coupling the capture element to a first extension of the implant to be placed, retracting the retrieval device and coupled implant extension back through the cannula channel so that the implant extension extends through the cannula, and removing the cannula to thereby leave in place in the first passage the implant extension.

The method may further include repeating the steps above on the opposite side of the patient's body to place a second implant extension. It may also further include the steps of slidably inserting the guide element into the cannula channel until the tissue penetrating tip extends out of the distal end of the cannula, passing the cannula and guide element through a second passage through a patient's pelvic cavity from a second external incision until the distal end of the guide element and cannula extend out through the vaginal incision, removing the guide element from the cannula by retracting it through the cannula channel, inserting the retrieval device through the cannula channel until the capture element passes out of the distal end of the cannula, coupling the capture element to a second extension of the implant, retracting the retrieval device and coupled second implant extension back through the cannula channel so that the implant extension extends through the cannula, and removing the cannula to thereby leave in place in the second passage the second implant extension.

These and other objects, features and advantages of the present invention will be apparent from the following detailed description of illustrative embodiments thereof, which is to be read in connection with the accompanying drawings.

DETAILED DESCRIPTION OF THE PREFERRED EMBODIMENTS

Although the present invention is described in detail in relation to particular implants for treating pelvic floor defects, it is to be understood that the invention is not so limited, as there are numerous other types and configurations of implants that could be placed using the assemblies and methods described herein.

Figure 1A:
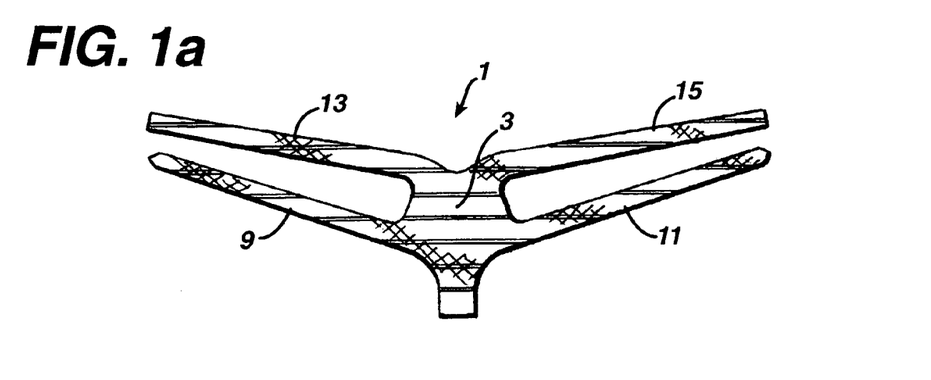
FIGS. 1a-1c illustrate exemplary meshes that can be placed using the system and method of the present invention.
Figure 1B:
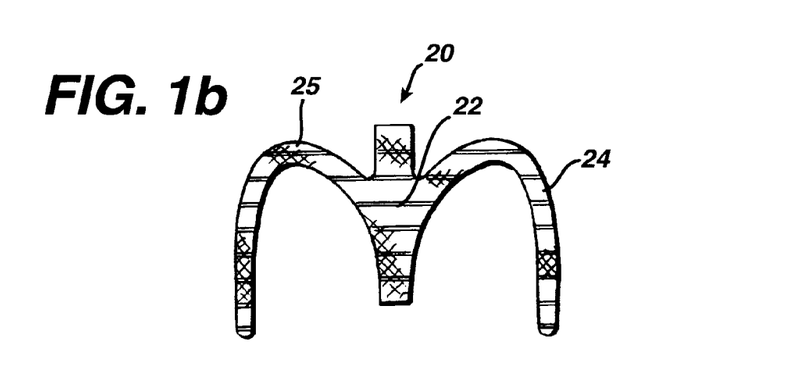
Figure 1C:
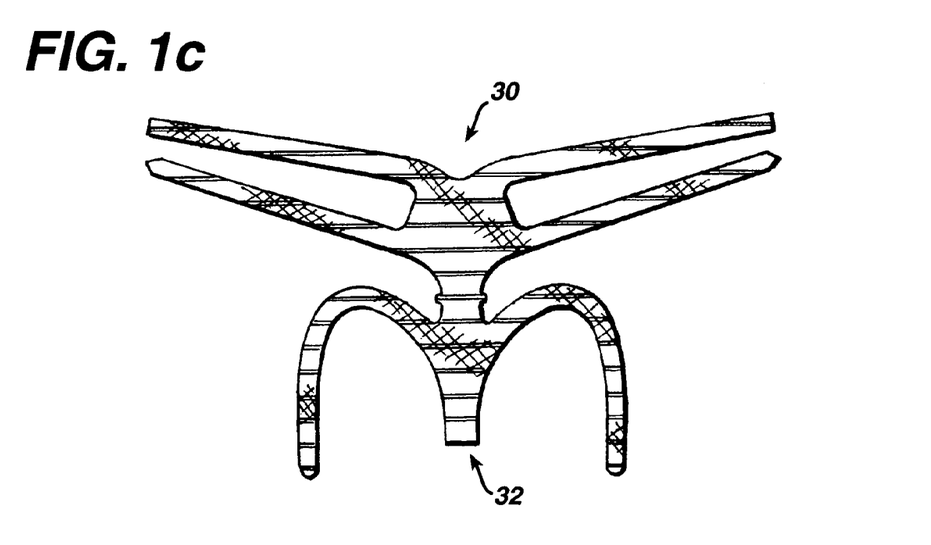
Figure 2:
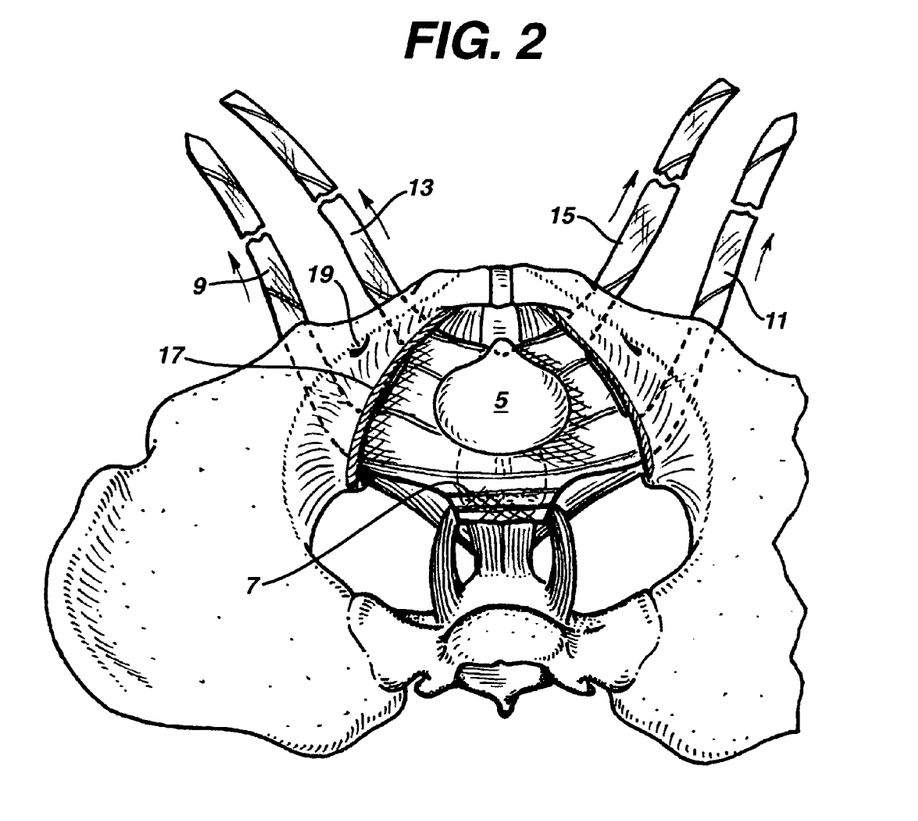
FIG. 2 illustrates the placement within the body of an exemplary mesh for treating a cystocele.
Figure 3:
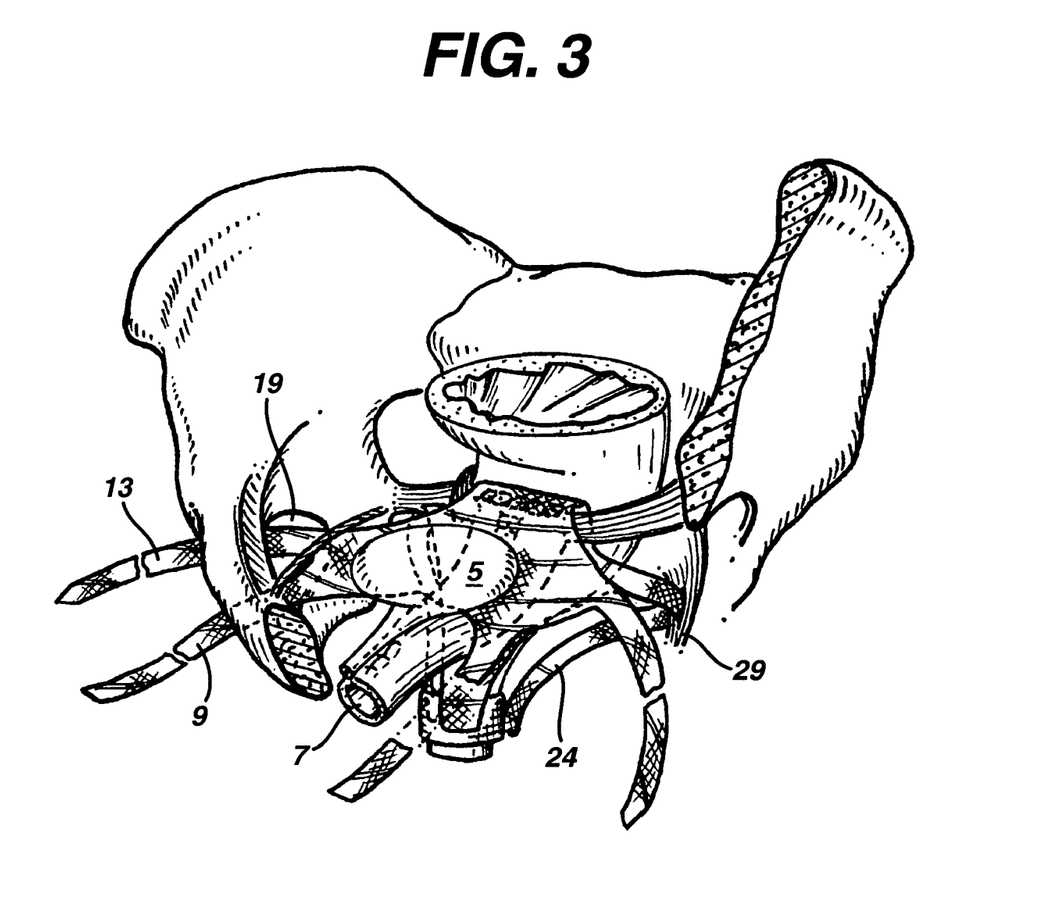
FIG. 3 illustrates the placement within the body of an exemplary mesh for treating both a cystocele and a rectocele.

FIGS. 1a-1c illustrate exemplary implants for use in pelvic floor repair that could be placed using the assemblies and methods described herein. FIG. 1a illustrates a mesh suitable for use in anterior or cystocele repair. The central portion 3 of the implant 1 is designed to be placed under low or no tension between the patient's urinary bladder 5 and vagina 7, to thereby reinforce the fascia in between and prevent the bladder from pushing down into the vagina, as is illustrated in FIG. 2. The implant 1 includes a first set of strap-like implant extensions 9, 11 and a second set of strap-like implant extensions 13, 15 extending outwardly from opposite sides of the implant. As shown in FIGS. 2 and 3, both sets of implant extensions, 9, 11; 13, 15 are designed to pass from a location in proximity to the patient's arcus-tendineous fascia pelvis (ATFP) 17, through the obturator membrane and out of the body through the obturator foramen 19. Passage of the implant extensions through tissue along the passages described above anchors the implant in place by means of friction and ultimately tissue ingrowth into the implant.

Figure 4:
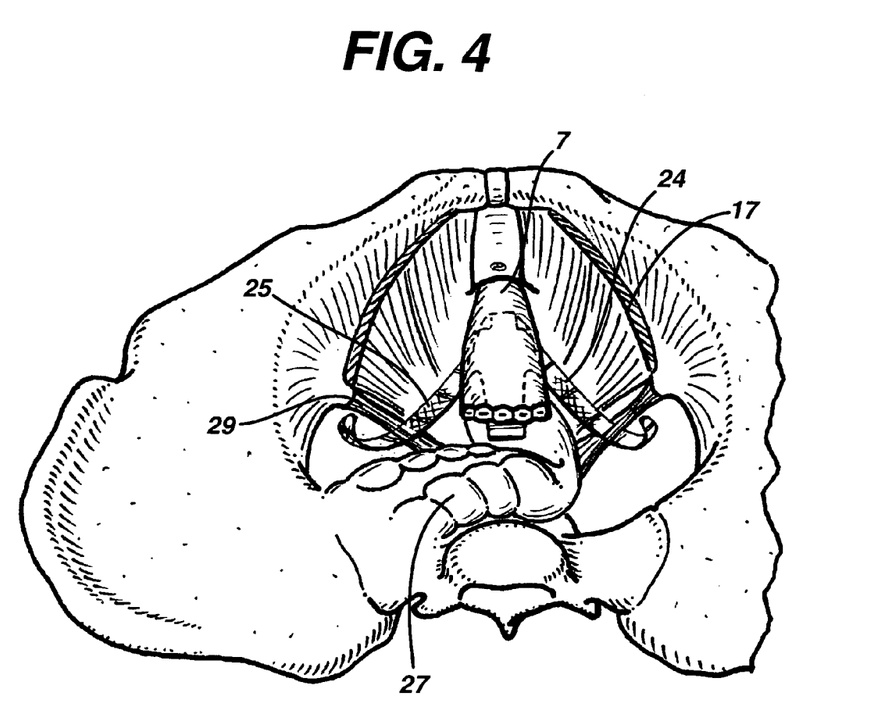
FIG. 4 illustrates the placement within the body of an exemplary mesh for treating a rectocele.

An exemplary implant for treating an apical, posterior/rectocele repair is shown in FIG. 1b. The implant 20 includes a central portion 22 that is designed to be placed under low or no tension between the patient's rectum 27 and vagina 7 (as shown in FIG. 4), reinforcing the fascia therebetween and preventing the rectum from pushing up into the vagina. The implant 20 includes two strap-like implant extensions 24, 25 extending outwardly therefrom in opposite directions. These implant extensions are designed to extend through the patient's sacro-spinous ligaments 29 and exit the body through the gluteous maximus in the vicinity of the anus as shown in FIG. 3.

FIG. 1c illustrates an implant that is suitable for both anterior and posterior repair when implanted as shown in FIG. 3. Each portion of the combination implant, the anterior portion 30 and the posterior portion 32, is substantially similar to that described above for separate implants. A suitable material for the implants described above is Gynecare's GYNEMESH™ PS, which is a knitted polypropylene mesh having a thickness of about 0.7 millimeters and which is manufactured by Ethicon, Inc., of Somerville, N.J. This material is approved by the FDA in the United States for implantation into the human body for a variety of uses.

As described above, difficulties exist with trying to place pelvic floor implants, and the present invention provides an improved assembly and method for doing so. The assembly consists of the components shown in FIGS. 5-7, and includes a guide element 52, a cannula 54, and a retrieval element 56. The guide element includes a handle 58 having any configuration suitable for grasping and manipulating the guide element, and a needle 60. The needle includes a tissue dissecting distal tip 62, which is preferably blunt but tapered, and preferably further includes a first substantially straight portion 66 extending from the handle, a curved transition portion 64 extending from the first substantially straight portion, and a second substantially straight portion 67 extending between the curved transitional portion and the distal tip 62. In a preferred embodiment, the length of the first substantially straight portion is approximately 75 mm, the length of the second substantially straight portion is approximately 10.6 mm, and the length of the curved portion is approximately 111 mm. Further, dimensions a and b shown in FIG. 5 are approximately 73 and 168 mm respectively, and the diameter of the needle is between 3 and 5 mm.

The needle must be substantially rigid such that it can resist yielding under forces that are normally experienced in passing the needle through the body as described herein. Various stainless steel alloys or titanium are materials suitable for this purpose. Suitable materials for the handle include steel, aluminum, titanium, plastic, rubber etc. In instances of a plastic handle, any standard manufacturing process can be used to form the handle, such as insert molding the handle to the needle, molding the handle in halves and press-fitting or using ultrasonic welding to connect the two handle pieces around the needle, etc.

Figures 5, 6, 7:
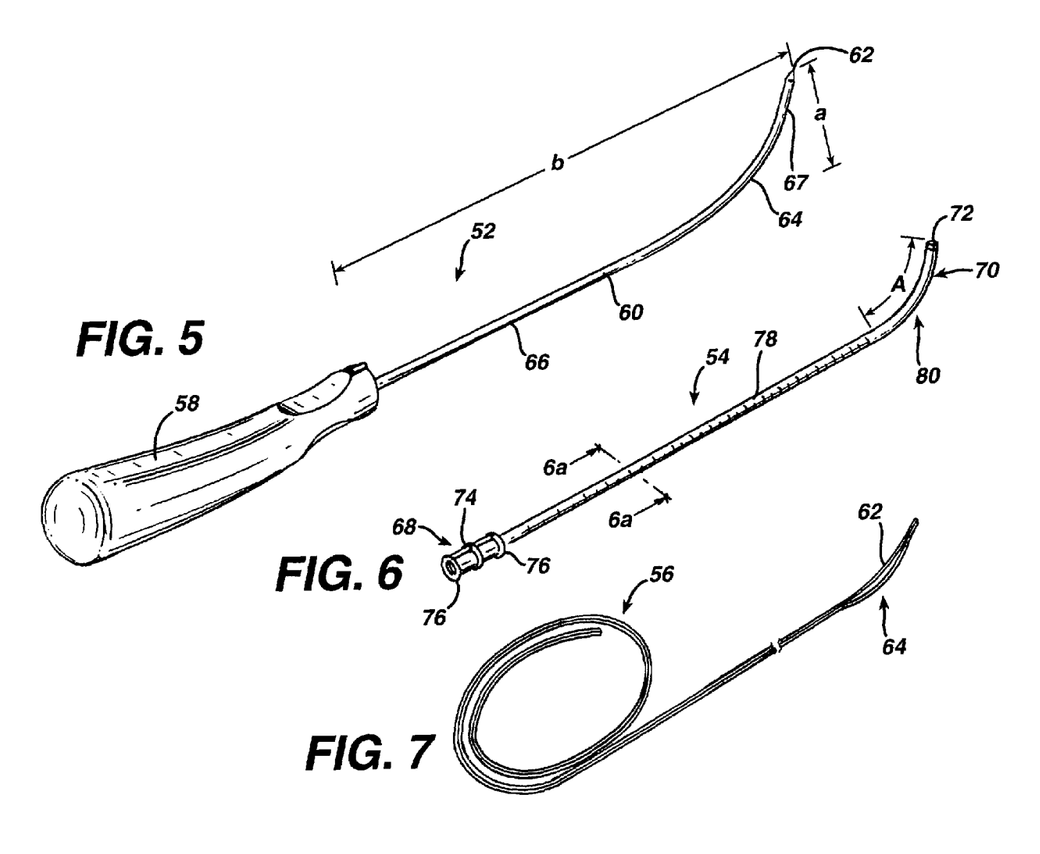
FIG. 5 illustrates an exemplary guide element of the assembly of the present invention.
FIG. 6 illustrates an exemplary cannula of the assembly of the present invention.
FIG. 7 illustrates an exemplary retrieval element of the assembly of the present invention.
Figures 6A, 6B, 8, 9A, 9B:
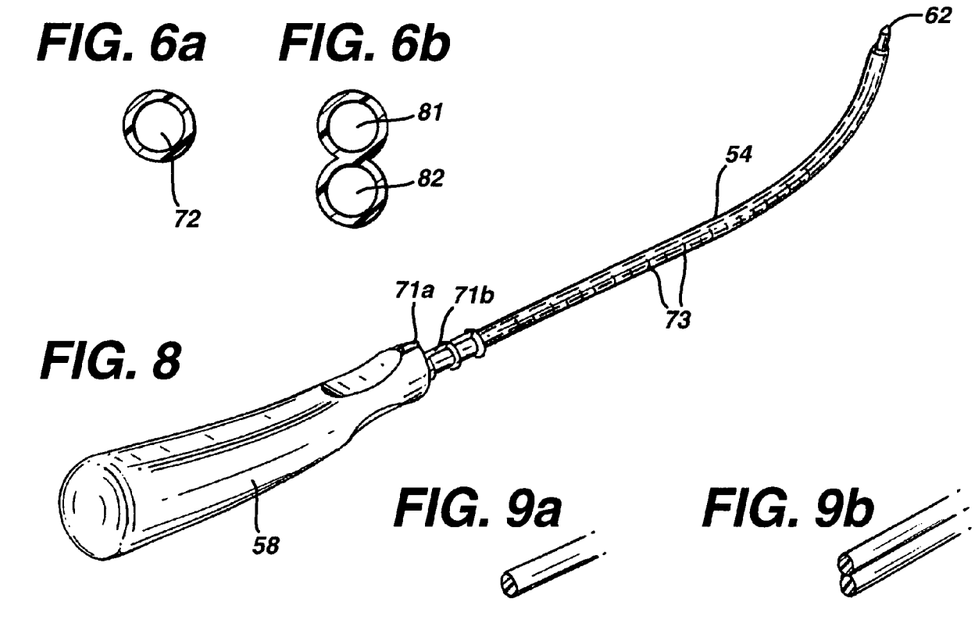
FIGS. 6a and 6b illustrate alternative exemplary cross-sectional configurations of the cannula of FIG. 6.
FIG. 8 illustrates the cannula of FIG. 6 inserted over the guide element of FIG. 5.
FIGS. 9a-9d illustrate various alternative cross-sectional configurations for the retrieval element of FIG. 7.

The cannula 54 is shown in FIG. 6, and preferably consists of a flexible or semi-rigid material and has a proximal end 68, a distal end 70 and a channel 72 extending therethrough between the proximal and distal ends. An enlarged hub portion 74 may exist at the proximal end, and may have one or more projections 76 extending outwardly therefrom. The hub and projections enable the surgeon to better handle the cannula and prevent the cannula from being pushed too far into the patient as will be described in greater detail below. The projections may also be designed in such a way that they secure the cannula in place within surrounding tissue. The cannula and guide element are dimensioned relative to one another so that the needle 60 of the guide element can be slidably received through the cannula channel 72 as shown in FIG. 8, with the tissue penetrating tip 62 of the guide element 52 extending outwardly from the distal end of the cannula. The distal end 70 of the cannula is preferably tapered so that there is a smooth transition from the distal tissue penetrating tip 62 of the guide element to the outer circumference 78 of the cannula as shown in FIG. 8. In this manner, trauma to surrounding tissue will be minimized during insertion of the cannula and guide element. Further, the diameter of the distal end of the cannula channel is preferably slightly smaller than that of the rest of the channel, and even slightly smaller than the diameter of the guide needle so that it dilates with insertion of the needle to form a snug fit between the guide needle and cannula. This can be accomplished by reducing the diameter of the channel at the distal end by secondary operations, or by the addition of a second material after production.

In a preferred embodiment, the cannula further includes a resilient end region 80 comprised of a resilient and sufficiently flexible material such that when the guide element is inserted within the cannula, the cannula assumes the configuration of the guide element as shown in FIG. 8. When the guide element is removed, however, the resilient end region 80 returns to a configuration that is different from, and more curved than that of the corresponding portion of the guide needle, as is shown in FIG. 6. This aspect is important in aiding passage of the retrieval device, as will also be described in greater detail below. This feature can be achieved by exposure to heat either before or after formation of the cannula, or simply by mechanical manipulation of the cannula such as placing it on a spool of a desired curvature. In one embodiment, the length of the hub portion 74 is approximately 18 mm, the length of the substantially straight portion is approximately 155 mm, the length $m_3$ of the resilient end region is approximately 35 mm with an angle A of approximately 80 degrees, and the length of the end region including the distal end is approximately 5 mm.

The cannula preferably is comprised of PEBAX™, which is a mixture of polyether and nylon, but may be constructed from or include various other materials such as polyethylene, Teflon, PVDF, PFE and Pebax. Other polymeric or non-polymeric materials with low coefficients of friction, such as flurorpolymers or hyluronic acid, may also be used to coat the inner and/or outer surfaces of the cannula in order to reduce friction between the cannula and guide needle and/or tissue. This material may be reinforced with a wire coil, plastic coil, or braid to increase stiffness or provide kink resistance. The hub may be comprised of a different material, such as foam, but could also be any hard or soft plastic, or elastomeric material such as urethane, rubber or silicone.

In addition, both the guide needle and cannula may each include a marking, bump or other feature 71*a*, 71*b* that are aligned with one another when the cannula is properly inserted over and oriented relative to the guide needle as shown in FIG. 8. In an alternate embodiment, the assembly may include a means for mechanically coupling the cannula and guide needle, such as a slot or notch in the needle or handle that mates with a corresponding element on the cannula. Other features that may be added include one or more radioopaque markings to enable visualization after placement using fluoroscopy or x-ray, or the addition of regularly spaced markings 73 along the length of the cannula to allow the user to determine how far the cannula has been inserted into the patient's body, and also to determine whether the cannula position has changed following its initial placement.

The cannula preferably has a substantially circular cross-section with a single channel therethrough as shown in FIG. 6*a*, but may be of any other suitable cross-sectional configuration. It may alternatively have two or more lumens, with one lumen providing for passage of the guide needle and a second provision for passage of the retrieval line.

The final element of the assembly is the retrieval line, which is shown in FIG. 7. In its most basic form, the retrieval element 56 is a flexible or semi-rigid elongate instrument having a capture element 62 at the distal end 64 that is suitable for capturing or securing thereto an implant extension portion of a mesh to be implanted. The retrieval element is dimensioned so that it (and the attached mesh implant extension portion) can be drawn through the cannula channel as will be described below. As shown in FIG. 7, in a preferred embodiment, the capture element is a simple loop through which the implant extension portion can be inserted so that it can be drawn through the cannula channel. Many other configurations for this capture element can also be envisioned, such as barb elements, various clips, cinching or lasso mechanisms etc., several of which are shown in FIGS. 10*a-d*.

The retrieval line may be made of any suitable material having sufficient rigidity such that it can be advanced through the cannula and out to a point where it is easily accessible by the surgeon. One suitable material is a polypropylene material such as PROLENE® (manufactured by Ethicon, Inc.) but many other semi-rigid plastics are suitable as well, such as acetal, ethylene tetrofluoroethylene, fluorinated ethylene propylene, high or low density polyethylene, nylon, polycarbonate, or polyurethane. In addition, stainless steel or nitinol are suitable as well.

Figure 9C:
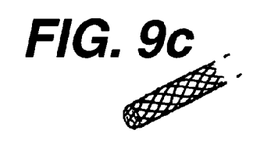
Figure 9D:
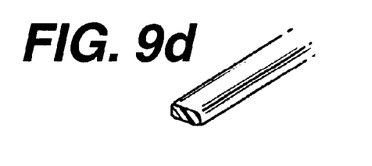

In one embodiment, the retrieval element is a simple monofilament extrusion having a substantially circular cross section as shown in FIG. 9*a*. In alternate embodiments, the retrieval element could be a tubular extrusion, a multi-lumen extrusion (FIG. 9*b*), a coiled wire similar to a stainless steel catheter guide wire, a braided configuration of plastic or stainless steel lines (FIG. 9*c*), or a single or multi-lumen extrusion having a cross-sectional shape other than substantially circular (FIG. 9*d*). One or more of the above could also be combined, for example to create a plastic coated wire, a mesh-reinforced tubing (with metal or plastic braided mesh), or dual extrusions with different plastics on different layers of extrusion.

Figure 10A:
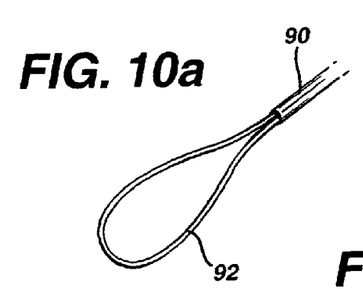
FIGS. 10a-10d illustrate various embodiments of a capture element of a retrieval element of the present invention.
Figure 10B:
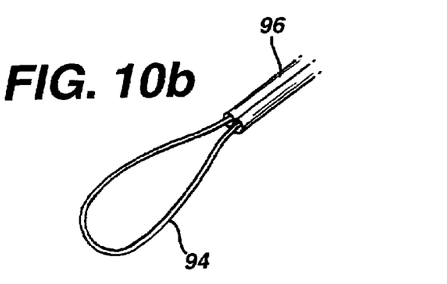
Figure 10C:
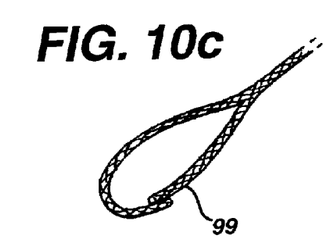
Figure 10D:
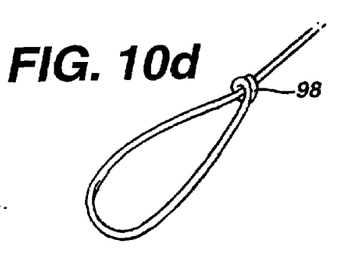

A preferred embodiment of the retrieval element is further illustrated in FIG. 10*a*, and includes a plastic tube 90 that is heat shrunk over a mono-filament loop 92 as described above. In alternative constructions, however, the mono-filament may simply be folded back on itself to form the loop and then welded together, or the mono-filament 94 can be inserted through a double lumen extrusion 96 (i.e., FIG. 10*b*). As indicated above, the retrieval element could alternatively include any suitable form of cinching mechanism 98 or mechanical capture mechanism 99 such as those illustrated in FIGS. 10*d* and 10*c* respectively.

Figure 11:
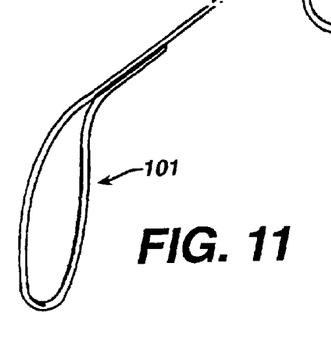
FIG. 11 illustrates a retrieval element according to the present invention including a capture element having a pre-formed curve.

Finally, the retrieval element also may include various features to render its use easier for the surgeon. For example, the retrieval line may include a pre-formed curve 101 at its distal end (FIG. 11), which is designed to point the retrieval line in a direction most easily accessible to the surgeon after it has been advanced through the cannula channel and has exited the vaginal incision. It may also include various features at the proximal end, such as graduated markings to indicate the degree of insertion, or handle features such as loops, balls etc. to facilitate grasping and holding of the proximal end of the retrieval line.

In an alternative embodiment, the cannula could be a dual channel cannula having a cross-section such as that shown in FIG. 6*b*. The first channel 81 would be dimensioned to receive the guide needle as described above, and the second channel 82 dimensioned to receive the retrieval line.

Preferred methods for using the surgical assembly of the present invention will now be described in detail. This method will be described in relation to insertion of a mesh such as that shown in FIG. 1*a* to repair a cystocele, but it is to be understood that this is illustrative only, as the assembly described herein can be used to place various types and configurations of meshes to repair various other pelvic floor defects or to improve upon various other medical conditions. Further, the methods described herein are exemplary, and other meshes may be placed in different manners and through different passageways using the assembly of the present invention.

Figure 12A:
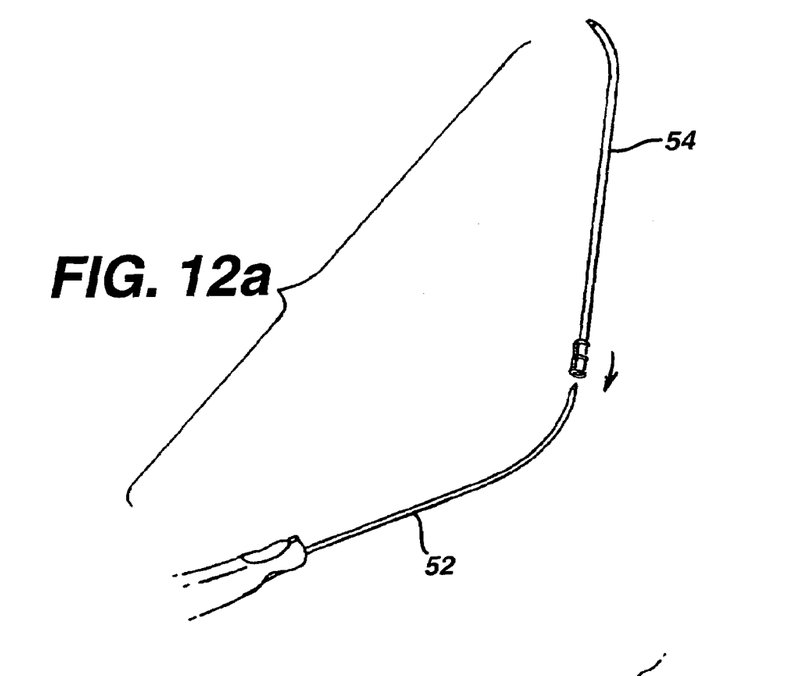
FIGS. 12a-12f illustrate various steps of a method for placing a surgical implant according to the present invention.
Figure 12B:
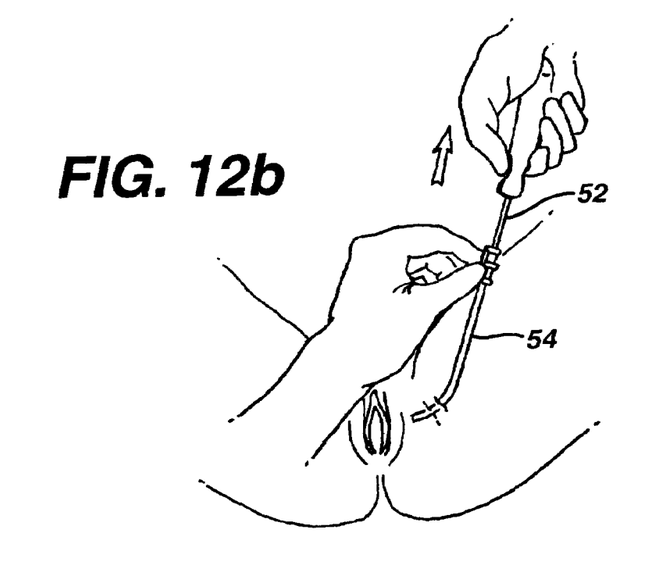

In preparation for inserting the implant of FIG. 1*a*, the full thickness of the anterior vaginal wall is incised as required and an appropriate associated lateral dissection is performed. The cutaneous S incision for the passage of mesh extension 13 is made in the skin over the anteromedial part of the obturator foramen, at the level of the urethral meatus. This incision should be approximately 4 mm long in order to enable the guide element 52 and cannula 54 to pass through the skin without tearing. The cannula 54 is, or has previously been, inserted over the guide needle 52 as shown in FIG. 12a until the tissue penetrating tip extends out from the distal end of the cannula as shown in FIG. 8. The cannula and guide element are then inserted through the incision, through the obturator membrane, and directed in a relatively direct path that results in the tip exiting the previously dissected space in the proper location as shown in FIG. 2. Once the distal tip of the guide element and cannula exit the vaginal dissection, the guide element is withdrawn from the cannula as shown in FIG. 12b, leaving the cannula in place in the body.

Figure 12C:
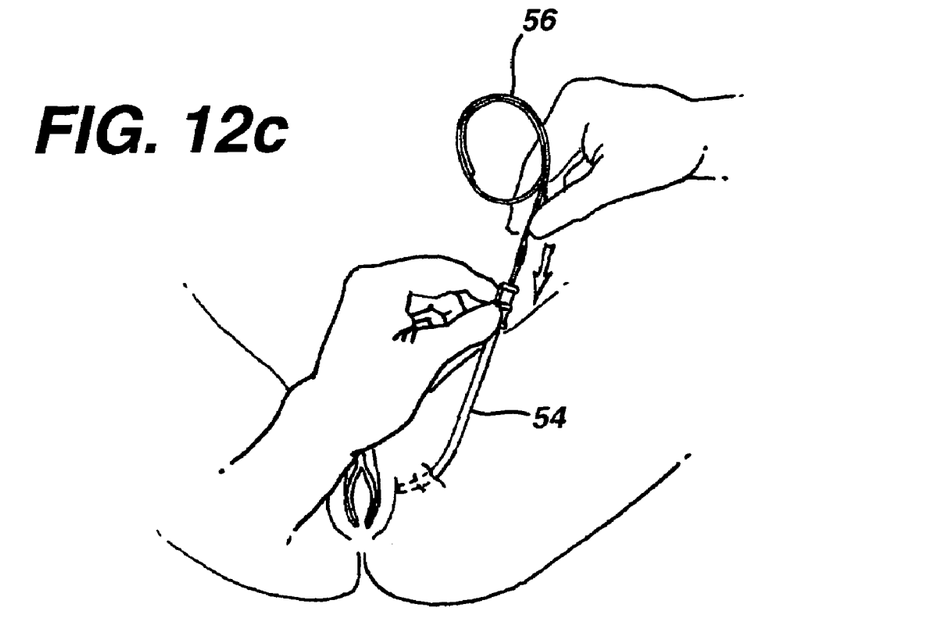
Figure 12D:
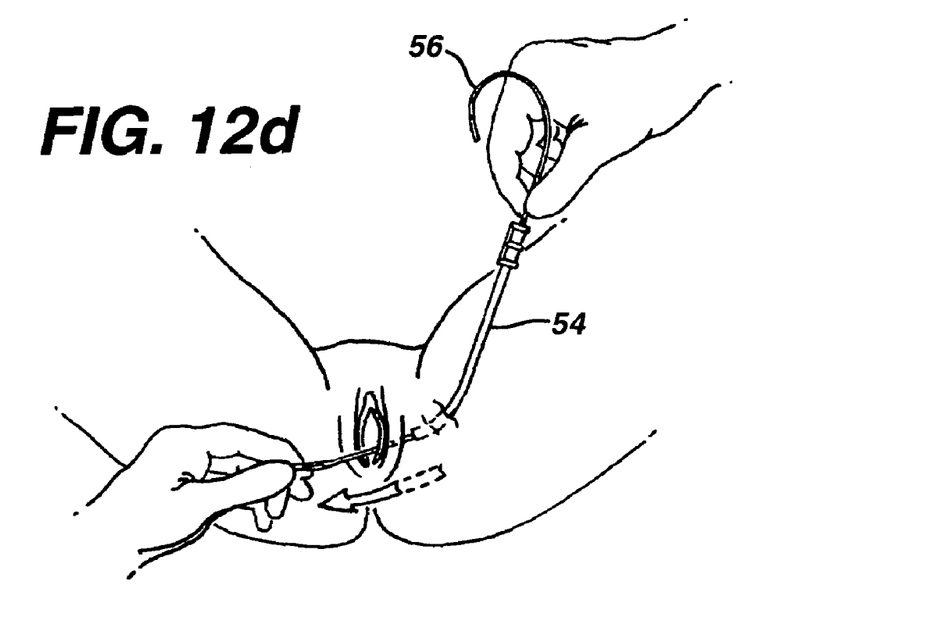
Figure 12E:
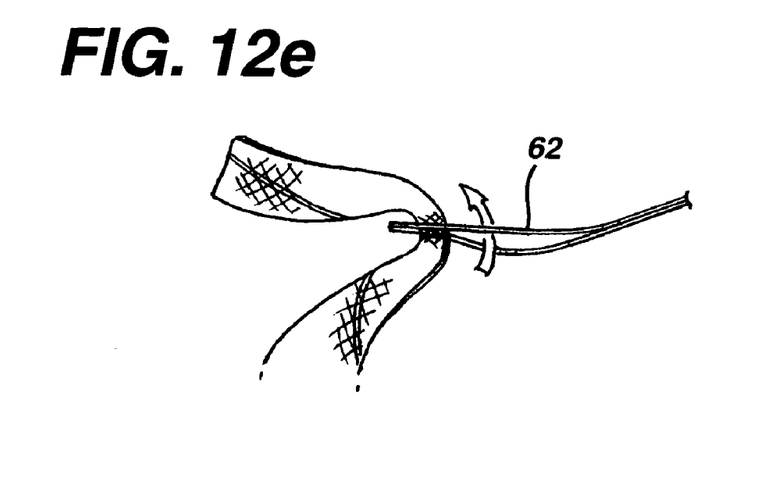
Figure 12F:
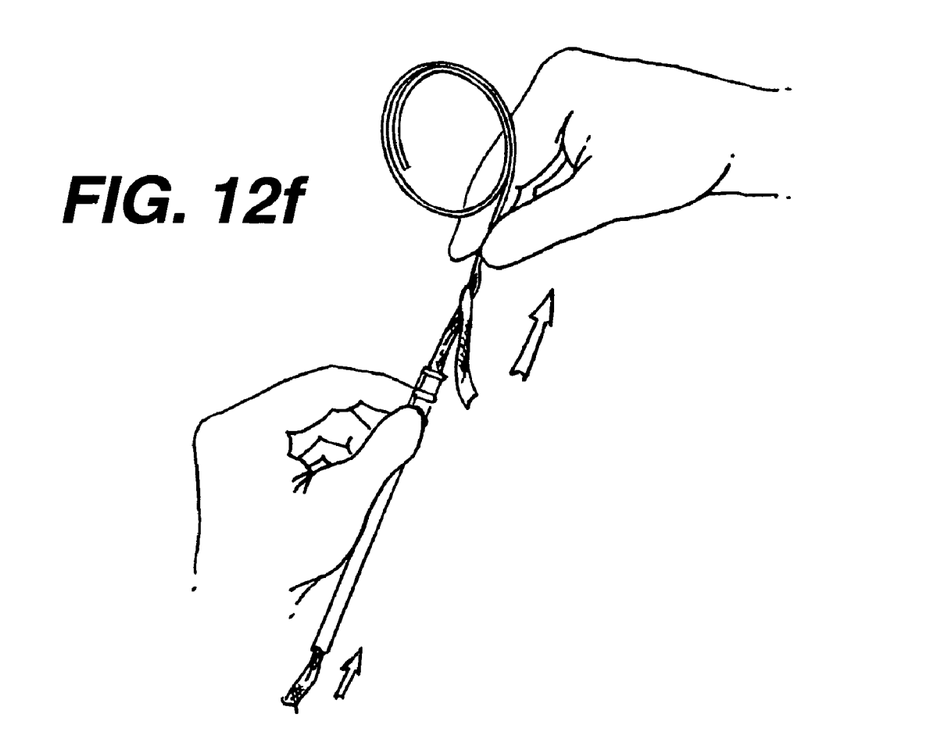

To pass implant extension 9, a second cutaneous incision is made at the level of the urethral meatus, approximately 3-4 cm below the preceding incision at the inferomedial part of the obturator foramen. The guide element and cannula are then inserted through the skin, through the obturator membrane on a path that allows it to emerge from the iliococcygeous muscle behind the ATFP approximately 1-1.5 cm from the ischial spine at the bottom of the paravesical fossa. Subsequently, retrieval elements are inserted through each of the placed cannulas, one at a time as shown in FIG. 12c, until the capture element exits the vaginal incision as shown in FIG. 12d. The surgeon then grasps the capture element, retrieves it out of the vagina, and passes implant extension 13 through the capture element as shown in FIG. 12e to thereby removably secure or couple the implant to the retrieval line. The retrieval line and the coupled implant extension are then retracted back through the cannula channel until the end of the implant extension exits the proximal end of the cannula as shown in FIG. 12f. Once all straps are passed out of the body, final adjustments are made. Subsequently, the cannulas are removed from the body, leaving the implant extensions extending through the passageways formerly occupied by the cannulas. The implant extensions are then trimmed in close proximity to the incisions. The tissue surrounding the implant extensions will in essence collapse in on the implant extensions, securing them in place and leading to ingrowth therein.

These steps are then repeated on the opposite side of the body to pass implant extensions 15, 11. The implant extensions are then trimmed in close proximity to the incisions in the upper leg and/or lower abdomen.

To place the posterior implant of FIG. 1b, the surgeon first performs an incision of the whole thickness of the posterior vaginal wall and an appropriate lateral dissection to expose the sacro-spinous ligament. Incisions are then made in the skin of the buttocks lateral to and below the anus and a cannula-loaded Guide is inserted into these incisions, exiting through the sacro-spinous ligament approximately 2 cm from the ischial spine. The guide is then removed and a retrieval line is installed and employed as described above for the anterior implant. As with the anterior implant, these operations are performed on both sides of the patient.

As indicated above, the retrieval line may include a preformed curve 101 (FIG. 11) at the distal end. This pre-formed curve renders the retrieval line easier to access by the surgeon once it exits the vaginal incision, since the curve can be configured to extend from the incision in a direction toward the surgeon. Similarly, the resilient end region 80 of the cannula may be configured so that, following removal of the guide needle, the resilient end region resumes a more curved configuration (i.e., FIG. 6) that points in a direction that facilitates passage of the retrieval line to the surgeon.

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention.

What is claimed is:

1. An assembly for placement of a surgical implant having at least one implant extension portion, the assembly comprising:
   a guide element having a tissue penetrating distal end;
   a cannula having a proximal end, a distal end, and a channel extending therethrough within which the guide element is slidably received such that the tissue penetrating tip of the guide element extends outward from the distal end of the cannula, wherein the cannula further includes a resilient end region that assumes a first shape when the guide element is received therein, and assumes a second shape when the guide element is removed from the cannula, the second shape having a greater curvature than the first; and
   a retrieval device having a capture element at a distal end thereof adapted to be coupled with the implant extension portion of the surgical implant,
   wherein the cannula having the guide element slidably received therein is dimensioned to extend through a patient's pelvic cavity from an external incision and out through a vaginal incision, and the cannula channel is dimensioned allow passage therethrough of the retrieval device and coupled implant extension portion.

2. The assembly according to claim 1, wherein when the guide element is received within the cannula channel, the guide element and cannula are dimensioned to form a substantially smooth transition from the tissue penetrating distal end of the guide element to an outer surface of the cannula.

3. The assembly according to claim 1, wherein the proximal portion of the cannula further includes an enlarged hub portion.

4. The assembly according to claim 3, wherein the hub portion further includes a plurality of projections extending outwardly therefrom.

5. The assembly according to claim 3, wherein the hub portion further includes a retrieval holding element for removably coupling the retrieval device to the cannula.

6. The assembly according to claim 1, wherein the distal end of the retrieval element includes a pre-formed curve.

7. An assembly for placement of a surgical implant having at least one implant extension portion, the assembly comprising:
   a guide element having a tissue penetrating distal end;
   a cannula having a proximal end, a distal end, and a channel extending therethrough within which the guide element is slidably received such that the tissue penetrating tip of the guide element extends outward from the distal end of the cannula; and
   a retrieval device having a capture element at a distal end thereof adapted to be coupled with the implant extension portion of the surgical implant,
   wherein the cannula having the guide element slidably received therein is dimensioned to extend through a patient's pelvic cavity from an external incision and out through a vaginal incision, and the cannula channel is dimensioned allow passage therethrough of the retrieval device and coupled implant extension portion, and wherein the capture element is a loop.

8. The assembly according to claim 1, wherein the capture element is a hook.

9. The assembly according to claim 1, wherein the cannula is dimensioned to extend between an external incision in the lower abdomen, or an external incision in the upper leg in proximity to the obturator foramen, and out through the vaginal incision.

10. A method for placing a surgical implant comprising the steps of:
providing an assembly including a guide element having a tissue penetrating distal end, a cannula having a proximal end, a distal end, a channel extending therethrough, and a resilient end region that assumes a first shape when the guide element is received therein, and assumes a second shape when the guide element is removed from the cannula, the second shape having a greater curvature than the first, and a retrieval device having a capture element at a distal end thereof;
slidably inserting the guide element into the cannula channel until the tissue penetrating tip extends out of the distal end of the cannula;
passing the cannula and guide element through a first passage through a patient's pelvic cavity from an external incision until the distal ends of the guide element and cannula extend out through a vaginal incision;
removing the guide element from the cannula by retracting it through the cannula channel;
inserting the retrieval device through the cannula channel until the capture element passes out the distal end of the cannula;
coupling the capture element to a first extension of the implant to be placed;
retracting the retrieval device and coupled implant extension back through the cannula channel so that the implant extension extends through the cannula; and
removing the cannula to thereby leave in place in the first passage the implant extension.

11. The method according to claim 10, further comprising repeating the steps of claim 10 on the opposite side of the patient's body to place a second implant extension.

12. The method according to claim 10, further comprising the steps of:
slidably inserting the guide element into the cannula channel until the tissue penetrating tip extends out of the distal end of the cannula;
passing the cannula and guide element through a second passage through a patient's pelvic cavity from a second external incision until the distal end of the guide element and cannula extend out through the vaginal incision;
removing the guide element from the cannula by retracting it through the cannula channel;
inserting the retrieval device through the cannula channel until the capture element passes out of the distal end of the cannula;
coupling the capture element to a second extension of the implant;
retracting the retrieval device and coupled second implant extension back through the cannula channel so that the implant extension extends through the cannula; and
removing the cannula to thereby leave in place in the second passage the second implant extension.

13. The method according to claim 12, further comprising repeating the steps of claim 12 on the opposite side of the patient's body to place third and fourth implant extensions.

14. The method according to claim 10, wherein the cannula further includes a resilient end region, wherein the resilient end region assumes a first shape when the guide element is received therein, and assumes a second shape when the guide element is removed from the cannula, the second shape having a greater curvature than the first.

15. The method according to claim 10, wherein the first passage extends from a first incision through the obturator foramen and obturator membrane and out through a vaginal incision.

16. The method according to claim 11, wherein the first passage extends from a first incision, through the obturator foramen and obturator membrane and out through a vaginal incision, and the second passage extends from a second incision, through the obturator foramen and obturator membrane, and out through the vaginal incision.

17. The assembly according to claim 7, wherein the capture element includes a pre-formed curve along at least a distal end thereof.

* * * * *